US007122318B2

(12) United States Patent
Ono et al.

(10) Patent No.: US 7,122,318 B2
(45) Date of Patent: Oct. 17, 2006

(54) METHOD FOR TESTING EFFECT OF ANGIOGENESIS INHIBITOR VIA INTEGRIN EXPRESSION INHIBITION

(75) Inventors: Naoto Ono, Ushiku (JP); Taro Senba, Ushiku (JP); Naoko Hata, Tsukuba (JP); Yasuhiro Funahashi, New York, NY (US); Toshiaki Wakabayashi, Tsukuba (JP)

(73) Assignee: Eisai Co., Ltd., Tokyo (JP)

( * ) Notice: Subject to any disclaimer, the term of this patent is extended or adjusted under 35 U.S.C. 154(b) by 361 days.

(21) Appl. No.: 10/468,615

(22) PCT Filed: Feb. 21, 2002

(86) PCT No.: PCT/JP02/01562

§ 371 (c)(1),
(2), (4) Date: Jan. 20, 2004

(87) PCT Pub. No.: WO02/066073

PCT Pub. Date: Aug. 29, 2002

(65) Prior Publication Data

US 2004/0132783 A1 Jul. 8, 2004

(30) Foreign Application Priority Data

Feb. 21, 2001 (JP) .............................. 2001-044646

(51) Int. Cl.
C12Q 1/68 (2006.01)
G01N 33/53 (2006.01)
(52) U.S. Cl. .......................................... 435/6; 435/7.1
(58) Field of Classification Search .................... 435/6, 435/7.1
See application file for complete search history.

(56) References Cited

U.S. PATENT DOCUMENTS

| 5,721,246 A | 2/1998 | Yoshino et al. ............. 514/300 |
| 5,843,906 A | 12/1998 | Chandrakumar et al. ..... 514/19 |
| 6,096,707 A | 8/2000 | Heino et al. .................. 514/12 |

FOREIGN PATENT DOCUMENTS

| EP | 1 074 542 | 2/2001 |
| EP | 1 258 252 | 11/2002 |
| WO | WO 98/44797 | 10/1998 |
| WO | WO 99/02551 | 1/1999 |
| WO | WO 00/41469 | 7/2000 |
| WO | WO 01/56607 | 8/2001 |
| WO | WO 02/066073 | 8/2002 |

OTHER PUBLICATIONS

Trikha, et al., "Human Prostate Carcinoma Cells Express Functional αIIbβ Integrin", *Cancer Research*, 56: 5071-5078, 1996.

Verheul, et al., "Vascular Endothelial Growth Factor-Stimulated Endothelial Cells Promote Adhesion and Activation of Platelets", *Blood*, 96: 4216-4221, 2000.
Verheul, et al., "Platelet and Coagulation Activation with Vascular Endothelial Growth Factor Generation in Soft Tissue Sarcomas", *Clinical Cancer Research*, 6: 166-171, 2000.
Baatout, et al., "Protein Content and Number of Nucleolar Organizer Regions are Enhanced During Phorbol Ester-Induced Differentiation of Cultured Human Megakaryocytic Cells", *Anticancer Research*, 19: 3229-3236, 1999.
Braun, et al., "Monoclonal Antibody Therapy with Edrecolomab in Breast Cancer Patients: Monitoring of Elimination of Disseminated Cytokeratin-Positive Tumor Cells in Bone Marrow", *Clinical Cancer Research*, 5: 3999-4004, 1999.
Brooks, et al., "Requirement of Vascular Integrin $\alpha_v\beta_3$ for Angiogenesis", *Science*, 264: 569-571, 1994.
Davis, et al., "An $\alpha2\beta1$ Integrin-Dependent Pinocytic Mechanism Involving Intracellular Vacuole Formation and Coalescence Regulates Capillary Lumen and Tube Formation in Three-Dimensional Collagen Matrix", *Experimental Cell Research*, 224: 39-51, 1996.
Denis, et al., "Pharmacodynamics and Pharmacokinetics of Bicalutamide: Defining an Active Dosing Regimen", *Urology*, 47: 26-32, 1996.
Eliceiri, et al., "Adhesion Events in Angiogenesis", *Current Opinion in Cell Biology*, 13: 563-568, 2001.
Friedlander, et al., "Definition of Two Angiogenic Pathways by Distinct $\alpha_v$ Integrins", *Science*, 270: 1500-1502, 1995.
Ikeda, et al., "Inhibition of Gelatinolytic Activity in Tumor Tissues by Synthetic Matrix Metalloproteinase Inhibitor: Application of Film in Situ Zymography", *Clinical Cancer Research*, 6: 3290-3296, 2000.
Nieuwenhuis, et al., "Human Blood Platelets Showing no Response to Collagen Fail to Express Surface Glycoprotein Ia" *Nature*, 318: 470-472, 1985.
Owa, et al., "Discovery of Novel Antitumor Sulfonamides Targeting G1 Phase of the Cell Cycle", *J. Med. Chem.* 42: 3789-3799, 1999.
Ozawa, et al., "E7070, A Novel Sulphonamide Agent with Potent Antitumour Activity in Vitro and In Vivo", *European Journal of Cancer*, 37: 2275-2282, 2001.
Senger, et al., "Angiogenesis Promoted by Vascular Endothelial Growth Factor: Regulation Through $\alpha_1\beta_1$ and $\alpha_2\beta1$ Integrins" *Proc. Natl. Acad. Sci. USA*, 94: 13612-13617, 1997.
Yoshino, et al., "Novel Sulfonamides as Potential, Systemically Active Antitumor Agents", *J. Med. Chem.* 35: 2496-2497, 1992.
Zutter, et al., "The Megakaryocyte/Platelet-Specific Enhancer of the $\alpha_2\beta1$ Integrin Gene: Two Tandem AP1 Sites and the Mitogen-Activated Protein Kinase Signaling Cascade", Blood, 93(5): 1600-1611, 1999.

(Continued)

*Primary Examiner*—Ethan Whisenant
(74) *Attorney, Agent, or Firm*—Brenda Herschbach Jarrell; Charles E. Lyon; Choate, Hall & Stweart, LLP (57) ABSTRACT

The present invention provides a system for testing the influence of a drug on integrin expression, which comprises measuring an integrin expression level in platelets of an individual to which the drug is administered and, based on the measured expression amount, determining what effect the drug has on integrin expression in cells other than platelets.

24 Claims, 3 Drawing Sheets

OTHER PUBLICATIONS

Zutter, et al., "Regulation of $\alpha_2$ Integrin Gene Expression in Cells with Megakaryocytic Features: A Common Theme of Three Necessary Elements", *Blood*, 86(8): 3006-3014, 1995, May 18, 2006.

Zutter, et al., "Binding of Phosphorylated Sp1 Protein to Tandem Sp1 Binding Sites Regulates $\alpha_2$ Integrin Gene Core Promoter Activity", *Blood*, 90(2): 678-689, 1997.

Zutter, et al., "The Human $\alpha_2$ Integrin Gene Promoter, Identification of Positive and Negative Regulatory Elements Important for Cell-Type and Developmentally Restricted Gene Expression", *The Journal of Biological Chemistry*, 269(1): 463-469, 1994.

International Search Report issued for corresponding PCT application PCT/JP02/01562.

METHOD FOR TESTING EFFECT OF ANGIOGENESIS INHIBITOR VIA INTEGRIN EXPRESSION INHIBITION

The present application is a United States National application filed under 35 USC 0 371 from, and claiming priority to, International Application PCT/JP02/01562, filed Feb. 21, 2002, which in turn claims priority to Japanese Application JP2001-44646, filed Feb. 21, 2001. The entire contents of each of these priority applications is incorporated herein by reference.

TECHNICAL FIELD

The present invention relates to a method for testing the effect of a drug that influences integrin expression, preferably an angiogenesis inhibitor.

BACKGROUND

Cancer is a disease showing high mortality, and the object of treatments with anticancer agents generally lies in improvement of the patient's quality of life ("QOL") and extension of survival time. However, it is difficult to determine the life prolongation effect of a drug in a short period of time, and therefore tumor reduction rate and blood tumor antigen level are often used as surrogate markers of the therapeutic effect of anticancer agents.

Further, since the life prolongation period for determining drug effect in clinical studies of anticancer agents requires a long-term study, tumor reduction rate, which can be evaluated in a relatively short period of time, has also been used as a surrogate marker. However, it has been pointed out that the tumor reduction rate cannot necessarily serve as an index of life prolongation. Accordingly, attempts have been made to use time to disease progression, length of disease free survival period, and/or biological markers etc. as surrogate markers. However, these methods have not yet been validated.

The following have been reported as surrogate markers:
1) Panorex, which is an antibody directed to glycoprotein EpCAM, was first identified as a tumor marker of colon cancer cells and was later found to be an adhesion molecule. Its correlation with survival rate is being examined to evaluate whether it can be used as a surrogate marker for elimination of microcarcinoma cells remaining in bone marrow (Stephan B. et al., Clinical Cancer Research, 1999, 5, 3999–4004) Large-scale phase-III clinical studies are being conducted in parallel.

2) The prostatic specific antigens have been used as a surrogate marker in hormone therapy of prostatic cancer to determine optimum doses (Denis L. & Mahler C. Urology, 1996, 47 (1A Suppl.), 26–32).

3) Matrix metalloprotease inhibitors have been tested as potential surrogate markers for angiogenesis inhibition. For example, a method of using BMS275291 has been examined in a phase I clinical trial as a potential surrogate marker for angiogenesis in wound healing (after a wound has been made in the skin. A method of using the enzymatic activity of a different metallproteinase inhibitor as a surrogate marker for angiogenesis at a tumor site has also been reported (Clin. Cancer Res., 2000, 6(8), 3290–6).

Angiogenesis inhibitors are expected to serve as effective therapeutic agents for diseases other than cancer. For example, such agents are expected to be useful in the treatment of arteriosclerosis, diabetic retinopathy, occlusion of retinal veins, retinopathy of prematurity, age-related macular degeneration, neovascular glaucoma, rheumatoid arthritis, juvenile rheumatoid arthritis, psoriasis, angioma, angiofibroma and so forth. If a surrogate marker of angiogenesis is found, it becomes possible to use that marker to determine, for example, a proper dose of a drug, an effect of a drug and/or a desirable administration protocol for a drug for each of these diseases.

Integrins are cell adhesion molecules expressed on a cell surface and composed of an α-chain and a β-chain. Integrins are involved in adhesion between extracellular matrix membrane proteins and cells, as well as in adhesion between cells. When a cell adhesion molecule binds to integrin, signal systems in the cell are initiated. As a result, not only cell adhesion, but also cell extension, cell growth, apoptosis, differentiation, cytoskeleton orientation, cell migration, tissue formation, cancer invasion and metastasis, wound healing, blood coagulation etc. occur.

Among the integrins, integrin α2β1 is known to act as an adhesion molecule on collagen, laminin and so forth, and also to be involved in the tube formation of vascular endothelial cells during angiogenesis (George E. et al., Exp. Cell. Res., 1996, 224, 39–51). Further, it has also been reported that antibodies directed to integrin α1 and integrin α2 inhibited the angiogenesis induced by VEGF in vivo (Donald R. S. et al., Proc. Natl. Acad. Sci. USA., 1997, 94, 13612–13617).

Integrin αvβ3 specifically exists in endothelial cells undergoing angiogenesis, and it has been reported that the integrin αvβ3 neutralizing antibody (LM609) inhibited the angiogenesis induced by fibroblast growth factor-2 (FGF-2) in an angiogenesis model utilizing chick embryo chorioallantois (Brook, P. C. et al., Science, 1994, 264, 569–571). Further, it has also been reported that integrin αvβ3 is involved in angiogenesis induced by FGF-2 and tumor necrosis factor-α, and that integrin αvβ5 is involved in angiogenesis induced by vascular endothelial growth factor (VEGF) and transforming growth factor-α (Friedlander, M. et al., Science, 1995, 270, 1500–1502). The anti-integrin αvβ3 antibody and the integrin αvβ3 inhibitor are currently in clinical studies.

SUMMARY OF THE INVENTION

The present invention provides a surrogate marker for inhibition of angiogenesis. In particular, the invention demonstrates that inhibition of integrin expression, preferably of integrin α2, acts as a surrogate marker for angiogenesis inhibition. Thus, according to the present invention, drugs that inhibit integrin expression inhibit angiogenesis.

The present invention provides the particular discovery that a drug represented by a compound of the general formula (II) (referred to as "Compound A" hereinafter), inhibits integrin α2 expression, and when such expression is inhibited, angiogenesis is also inhibited. Thus, according to the present invention, cancer cell growth is inhibited by Compound A, which inhibits angiogenesis via inhibition of integrin α2 expression. The present invention also demonstrates that integrin α2 expression on the surfaces of platelets in peripheral blood was decreased when angiogenesis was inhibited.

They further found that the integrin α2 amount on the surfaces of platelets in peripheral blood was useful as a surrogate marker of angiogenesis inhibition, and thus accomplished the present invention.

That is, the present invention provides the followings:
1. A method for testing influence of a drug on integrin expression, which comprises the step of measuring an integrin expression amount in platelets of a patient to which the drug is administered and the step of determining influence of the drug on integrin expression in cells other than platelets based on the measured expression amount.
2. The method according to 1, wherein the integrin is integrin α2.
3. The method according to 1, wherein the integrin expression amount is measured by an immunochemical method.
4. The method according to 3, wherein the immunochemical method is an FACS method.
5. A reagent for quantifying integrin, for use in the method as defined in 3.
6. The method according to 1, wherein the integrin expression amount is measured by measuring an amount of mRNA coding for the integrin.
7. The method according to 6, wherein the amount of mRNA is measured by quantitative PCR.
8. A reagent for quantifying mRNA coding for integrin, for use in the method as defined in 6.
9. The method according to 2, wherein the drug is a sulfonamide compound represented by the general formula (I):

wherein
B represents a C6–C10 aryl ring or a 6- to 10-membered heteroaryl ring, each of which may be substituted and partially saturated;
K represents a single bond, —CH=CH— or —(CR$^{4b}$R$^{5b}$)$_{m^b}$— wherein R$^{4b}$ and R$^{5b}$ may be the same or different and each represent a hydrogen atom or C1–C4 alkyl, and m$^b$ is an integer of 1 or 2;
R$^1$ represents a hydrogen atom or C1–C6 alkyl;
Z represents a single bond or —CO—NH—; and
R represents a C6–C10 aryl ring or a 6- to 10-membered heteroaryl ring, each of which may be substituted and partially saturated; or
a pharmacologically acceptable salt thereof, or a hydrate thereof.
10. The method according to 9, wherein R represents indole, quinoline or isoquinoline.
11. The method according to 2, wherein the drug is a sulfonamide compound represented by the general formula (I$^a$):

wherein
A$^a$ represents a monocyclic or bicyclic aromatic ring which may be substituted;
B$^a$ represents a 6-membered unsaturated hydrocarbon ring or an unsaturated 6-membered heterocycle containing one nitrogen atom as a heteroatom, each of which may be substituted;
C$^a$ represents a 5-membered heterocycle containing one or two nitrogen atoms which may be substituted;
R$^{1a}$ represents a hydrogen atom or C1–C6 alkyl;
W$^a$ represents a single bond or —CH=CH—;
Y$^a$ represents a carbon or nitrogen atom;
Z$^a$ represents —N(R$^{2a}$)— wherein R$^{2a}$ represents a hydrogen atom or lower alkyl, or a nitrogen atom; or
a pharmacologically acceptable salt thereof, or a hydrate thereof.
12. The method according to 11, wherein W$^a$ represents a single bond.
13. The method according to 11, wherein W$^a$ represents a single bond, Z$^a$ represents —NH—, and Y$^a$ represents a carbon atom.
14. The method according to any one of 11 to 13, wherein B$^a$ represents benzene or pyridine which may be substituted.
15. The method according to any one of 11 to 14, wherein C$^a$ represents pyrrole which may be substituted.
16. The method according to 11, wherein A$^a$ represents benzene or pyridine which may be substituted, B$^a$ represents benzene which may be substituted, C$^a$ represents pyrrole which may be substituted, W$^a$ represents a single bond, and Z$^a$ represents —NH—.
17. The method according to 2, wherein the drug is a heterocyclic compound containing sulfonamide represented by the general formula (I$^b$):

wherein
A$^b$ represents a hydrogen atom; a halogen atom; hydroxyl; C1–C4 alkyl or alkoxy which may be substituted with a halogen atom; cyano; —(CO)$_{k^b}$NR$^{2b}$R$^{3b}$ wherein R$^{2b}$ and R$^{3b}$ may be the same or different and each represent a hydrogen atom or C1–C4 alkyl which may be substituted with a halogen atom, and k$^b$ is 0 or 1; C2–C4 alkenyl or alkynyl which may be substituted; or phenyl or phenoxy which may have a substituent selected from Group A mentioned below;
B$^b$ represents aryl or monocyclic heteroaryl which may have a substituent selected from Group A mentioned below, or wherein $Q^b$ represents an aromatic ring which may have one or two nitrogen atoms, $M^b$ represents a C5–C12 unsaturated monocyclic or polycyclic ring sharing a double bond with $Q^b$, which may have one to four heteroatoms selected from a nitrogen atom, an oxygen atom and a sulfur atom, $Q^b$ and $M^b$ may share a nitrogen atom, and $Q^b$ and $M^b$ may have a substituent selected from Group A mentioned below;

$K^b$ represents a single bond or —$(CR^{4b}R^{5b})m^b$— wherein $R^{4b}$ and $R^{5b}$ may be the same or different and each represent a hydrogen atom or C1–C4 alkyl, and $m^b$ is an integer of 1 or 2;

$T^b$, $W^b$, $X^b$ and $Y^b$ may be the same or different and each represent $=C(D^b)$— wherein $D^b$ represents a hydrogen atom, a halogen atom, hydroxyl, C1–C4 alkyl or alkoxy which may be substituted with a halogen atom, cyano, —$(CO)_{r^b}NR^{6b}R^{7b}$ wherein $R^{6b}$ and $R^{7b}$ may be the same or different and each represent a hydrogen atom or C1–C4 alkyl which may be substituted with a halogen atom, and $n^b$ is 0 or 1, or C2–C4 alkenyl or alkynyl which may be substituted; or a nitrogen atom;

$U^b$ and $V^b$ may be the same or different and each represent $=C(D^b)$— wherein $D^b$ has the same meaning as defined above, a nitrogen atom, —$CH_2$—, an oxygen atom or —$CO$—;

$Z^b$ represents a single bond or —$CO$—$NH$—;

$R^{1b}$ represents a hydrogen atom or C1–C4 alkyl;

— represents a single bond or a double bond:

Group A: a halogen atom; hydroxyl; C1–C4 alkyl or alkoxy which may be substituted with a halogen atom; cyano; —$R^{8b}R^{9b}N(NH)_p{}^b$— wherein $R^{8b}$ and $R^{9b}$ may be the same or different and each represent a hydrogen atom or C1–C4 alkyl which may be substituted with a halogen atom, and $p^b$ is 0 or 1, $R^{8b}$ and $R^{9b}$ may form a 5- or 6-membered ring together with a nitrogen atom to which they bond, and this ring may further contain a nitrogen atom, an oxygen atom or a sulfur atom and may be substituted; aminosulfonyl which may be substituted with mono- or di-(C1–C4 alkyl); C1–C8 acyl which may be substituted; (C1–C4 alkyl)-$S(O)_s{}^b$—(C1–C4 alkylene) wherein $s^b$ is an integer of 0, 1 or 2; C1–C4 alkyl or phenylsulfonylamino which may be substituted; —$(CO)_q{}^bNR^{10b}R^{11b}$ wherein $R^{10b}$ and $R^{11b}$ may be the same or different and each represent a hydrogen atom or C1–C4 alkyl which may be substituted with a halogen atom or amino which may be substituted with C1–C4 alkyl, and $q^b$ is 0 or 1; or aryl or heteroaryl which may be substituted; or a pharmacologically acceptable salt thereof, or a hydrate thereof.

18. The method according to 17, wherein $U^b$ and $V^b$ each represent $=C(D^b)$— wherein $D^b$ has the same meaning as defined above, or a nitrogen atom.

19. The method according to 17 or 18, wherein $Z^b$ represents a single bond.

20. The method according to any one of 17 to 19, wherein at least one of $T^b$, $U^b$, $V^b$, $W^b$, $X^b$ and $Y^b$ represents a nitrogen atom.

21. The method according to any one of 17 to 20, wherein $A^b$ represents a halogen atom; C1–C4 alkyl or alkoxy which may be substituted with a halogen atom; cyano; —$(CO)_{r^b}NR^{12b}R^{13b}$ wherein $R^{12b}$ and $R^{13b}$ may be the same or different and each represent a hydrogen atom or C1–C4 alkyl which may be substituted with a halogen atom, and $r^b$ is 0 or 1; or C2–C4 alkenyl or alkynyl which may be substituted.

22. The method according to any one of 17 to 21, wherein only one of $T^b$, $U^b$, $V^b$, $W^b$, $X^b$ and $Y^b$ represents a nitrogen atom.

23. The method according to any one of 17 to 22, wherein only one of $T^b$, $W^b$ and $Y^b$ represents a nitrogen atom.

DETAILED DESCRIPTION OF CERTAIN PREFERRED EMBODIMENTS

The present invention provides a method for testing influence of a drug on integrin expression, which comprises the step of measuring an integrin expression amount in platelets of an individual to which the drug is administered, based on the measured expression amount, determining what influence of the drug has on integrin expression in cells other than platelets.

The integrin is preferably integrin α2. Integrin α2 is one of the members of the integrin family of adhesion molecules expressed on cell surfaces. The sequence of human integrin α2 is registered at the GenBank with Accession No. NM_002203.

Compound A mentioned above decreases integrin α2 expression, in particular, and exhibits angiogenesis inhibitory action and anti-tumor growth action. Therefore, effect of a drug represented by Compound A can be determined with higher sensitivity by measuring the integrin α2 expression amount on platelets.

Doses and methods for administering a drug to a patient are not particularly limited, and those suitable for the purpose of the drug may be used. The method of the present invention is preferably used to test influence of a drug administered by systemic administration such as oral administration.

According to the present invention, integrin expression levels on platelets may be used as a surrogate marker for integrin expression levels in any of a variety of other cell types, preferably including cells of a tissue in which angiogenesis can occur. For example, platelet integrin levels may be detected in lieu of integrin levels in vascular endothelial cells of tumor tissue. Alternatively or additionally, platelet integrin levels may be detected in lieu of integrin levels in fibroblasts or tumor cells, for example, melanoma cells, in which signals such as those for cell growth, apoptosis and differentiation are transmitted via integrin α2. Further, since integrin α2 expression has been confirmed in monocytes, B cells and T cells, expression levels in platelets can also serve as a surrogate marker for expression levels in these cells.

The method of the present invention is also useful to estimate functions of these cells.

The method for measuring an integrin expression amount in platelets is not particularly limited. The integrin expression amount may be measured by an immunochemical method or the like, or an amount of mRNA coding for integrin may be measured.

Examples of the method for measuring integrin expression amount based on an immunochemical method include an FACS method. The FACS method is a method of measuring fluorescence intensity or the like of cells immunochemically stained with fluorescence-labeled antibodies by using a fluorescence activated cell sorter.

Examples of the method for measuring amount of mRNA coding for an integrin protein include quantitative PCR Hereafter, an embodiment of the step of measuring expression amount will be explained in detail in the order of 1. isolation of platelets, 2. quantification of integrin amount on platelet surfaces and 3. quantification of integrin mRNA amount in platelets.

1. Isolation of Platelets.

Platelets can be isolated by techniques of centrifugation, gel filtration, flow cytometry and so forth.

1) Centrifugation: To blood, 10% volume of 3.8% sodium citrate aqueous solution is added and the mixture is centrifuged at 100×g at room temperature for 10 minutes. The upper layer is used as platelet-rich plasma and centrifuged at 1500×g for 10 minutes. Platelets are obtained from the precipitates.

2) Flow cytometry: Blood diluted with PBS or the like is flown in a flow cytometer and exposed to a laser beam or a similar beam. Platelets can be isolated from other blood cells based on intensities of forward scattering light and side scattering light generated at that time.

2. Quantification of Integrin Amount on Platelet Surfaces

The amount of integrin present on platelet surfaces can be quantified by an immunochemical method, for example, immunohistological staining, ELISA, western blotting, flow cytometry and so forth. In ELISA, for example, platelets are bound to a solid phase via antibodies directed to a platelet surface antigen and thereby immobilized on the solid phase, and washed. Then, labeled anti-integrin antibodies are reacted therewith, and integrin on the platelet surfaces can be quantified from the amount of the binding labels. In Western blotting, for example, isolated platelets are solubilized in a buffer containing SDS and then subjected to SDS-PAGE and Western blotting. The integrin blotted on a membrane can be quantified by using labeled anti-integrin antibodies. In this case, if the amount of platelets is quantified by using antibodies directed to a platelet surface antigen at the same time, the amount of integrin per platelet can also be quantified.

In flow cytometry, for example, whole blood is diluted and bound with labeled anti-integrin antibodies. A platelet fraction can be isolated based on forward scattering light and side scattering light, and the integrin amount on platelets can be quantified by measuring the fluorescence intensity on platelets. Flow cytometry will be specifically explained below, but the scope of the present invention is not limited by the explanation. By using flow cytometry, integrin amount can be quantified by using whole blood without isolating platelets.

4 µl of blood is diluted with 396 µl of PBS containing 0.0038% sodium citrate aqueous solution. Antibodies directed to integrin labeled with FITC, preferably antibodies directed to integrin α2, for example, FITC-labeled anti-mouse CD49b antibodies (BD Pharmingen, Cat. No. BD-558757) in the case of a mouse, or FITC-labeled anti-human CD49b antibodies (BD Pharmingen, Cat. No. BD-555498) in the case of human, are diluted with PBS containing 0.1% BSA to an appropriate concentration. 10 µl of the antibodies are added to 90 µl of the diluted blood. The mixture is allowed to react at room temperature for 60 minutes and passed through a filter (FALCON, Cat. No. 2235). To the residue, 900 µl of PBS is added, and a platelet fraction is isolated based on intensities of forward scattering light and side scattering light measured by using a flow cytometer (Becton Dickinson, FACS Calibur). Integrin, preferably integrin α2, on platelets is quantified by measuring fluorescence intensity on platelets.

3. Quantification of Integrin mRNA Amount in Platelets

1) Extraction of RNA: RNA can be extracted by the guanidine thiocyanate method, phenol method or the like. The isolated platelets are dissolved in 1 ml of ISOGEN and left at room temperature for 5 minutes. To the mixture, 0.2 ml of chloroform is added, and the mixture is stirred and then left for 2 minutes. The reaction mixture is centrifuged at 4° C. for 15 minutes at 13000 rpm (MX-150, TOMY, Rotor TMA-11), and the supernatant is transferred to anther tube. 0.5 ml of isopropanol is added and the mixture is left at room temperature for 5 minutes. The mixture is centrifuged at 13000 rpm at 4° C. for 10 minutes (MX-150, TOMY, Rotor TMA-11), and the supernatant is discarded. To the precipitates, 1 ml of 70% aqueous ethanol solution is added and the mixture is centrifuged at 15000 rpm at 4° C. for 15 minutes (MX-150, TOMY, Rotor TMA-11). The supernatant is discarded, and the precipitates are dissolved in RNase-free $H_2O$.

2) Quantification of RNA: RNA can be quantified by techniques of Northern blotting analysis, dot blotting analysis, RNase protection assay, comparative RT-PCR, competitive RT-PCR, quantitative PCR and so forth. Quantitative PCR is preferred. The quantitative PCR technique will be explained below, but the scope of the present invention is not limited by the explanation. Quantitative PCR is performed as follows by using TaqMan Probe and ABI Prism 7700 Sequence Detection System (Perkin-Elmer Applied Biosystems).

The operation is performed with two steps of reverse transcription reaction and PCR. The reverse transcription reaction of the first step is carried out by adding dNTP, oligo $d(T)_{16}$ primer, RNase inhibitor and Multiscribe Reverse Transcriptase (Perkin-Elmer Applied Biosystems) to the obtained RNA, keeping the mixture at 25° C. for 10 minutes and then heating the mixture at 48° C. for 30 minutes. The mixture is heated at 95° C. for 5 minutes to terminate the reaction.

The obtained cDNA is used in PCR of the second step. PCR is carried out in, for example, a reaction system comprising 2.5 ng of cDNA, 1×TaqMan PCR buffer, 3 mM $MgCl_2$, 200 µM each of dATP, dCTP and dGTP, 400 µM dUTP, 200 nM primer pair, 0.01 U/µl of AmpErase UNG, and 0.025 U/µl of AmpliTaq Gold DNA Polymerase (Perkin-Elmer Applied Biosystems). As for the reaction conditions, reactions are performed at 50° C. for 2 minutes and 95° C. for 10 minutes followed by a cycle consisting of reactions at 95° C. for 20 seconds, at 55° C. for 20 seconds and at 72° C. for 30 seconds, which is repeated 40 times. The primers and the probe are designed by using Primer Expression (Perkin-Elmer Applied Biosystems). For comparison of two or more specimens, quantified values are used after correction based on mRNA level of a house keeping gene, which shows little variation in transcription amount in each specimen, preferably mRNA level of GAPDH.

The effect of a drug on integrin expression in cells other than platelets is determined by inference from the expression amount measured as described above. This inference is based on the correlation of integrin expression amount in platelets with integrin expression amount in cells other than platelets. That is, if the expression amount in platelets declines, the drug can be determined to exhibit influence of declining the integrin expression in cells other than platelets. Conversely, when the expression amount in platelets increases, the drug can be determined to exhibit influence of increasing the integrin expression in cells other than platelets.

Further, the present invention also provides a quantification reagent for use in the method of the present invention.

In one embodiment, the quantification reagent is an immunochemical reagent for quantifying integrin expression on platelets, and thereby determining the effect of a drug on integrin expression and/or angiogenesis.

The components of the quantification reagent of this embodiment may be similar to reagents for use in immunochemical quantification of integrin. The quantification reagent of this embodiment can be produced by a technique selected from those conventionally used in the production of quantification reagents depending on the measurement method based on an immunochemical method. Usually, an anti-integrin antibody is included. The anti-integrin antibody may be labeled with a fluorescent substance.

When the quantification reagent is constituted by two or more components, it may be provided as a kit. Further, the quantification reagent may be provided as a composition further containing a carrier acceptable in use of the quantification reagent. For example, the kit may include a fluorescence-labeled monoclonal antibody directed to integrin α2 or a monoclonal antibody directed to integrin α2 and a fluorescence-labeled anti-mouse Ig antibody, a diluent and an immobilization solution.

In another embodiment, the quantification reagent is one useful in measuring the amount of mRNA coding for the integrin.

The components of the quantification reagent of this embodiment may be similar to those of reagents used in quantification of mRNA coding for integrin. The quantification reagent of this embodiment can be produced by a technique selected from those conventionally used in the production of quantification reagents based on the mRNA quantification method. Examples of the method include those based on PCR, hybridization etc. Usually, the reagent includes a nucleic acid complementary to mRNA coding for integrin, which can be used as a primer or a probe. Primers and probes can be readily designed by those skilled in the art based on the nucleotide sequences coding for known integrins.

When the quantification reagent is constituted by two or more components, it may be provided as a kit. Further, the quantification reagent may be provided as a composition further containing a carrier acceptable in use of the quantification reagent. For example, the kit may include PCR primers, preferably labeled primers for quantitative PCR, a control primer and control DNA.

The drug is preferably a sulfonamide compound represented by the general formula (I), (I$^a$) or (I$^b$), or a pharmacologically acceptable salt thereof, or a hydrate of them.

The C6–C10 aryl ring or 6- to 10-membered heteroaryl ring represented by B and R in the general formula (I), which may be substituted and partially saturated, means an aromatic hydrocarbon group having 6 to 10 carbon atoms or a 6- to 10-membered aromatic heterocycle containing at least one of a nitrogen atom, an oxygen atom and sulfur as a heteroatom, each of which may have one or more substituents thereon and be partially saturated. Specific examples thereof include benzene, pyridine, pyrimidine, pyrazine, pyridazine, naphthalene, quinoline, isoquinoline, phthalazine, naphthyridine, quinoxaline, quinazoline, cinnoline, indole, isoindole, indolizine, indazole, benzofuran, benzothiophene, benzoxazole, benzimidazole, benzopyrazole, benzothiazole, 4,5,6,7-tetrahydroindole, 1,2,3,4-tetrahydroisoquinoline, 2,3-dihydrobenzofuran, indane, tetralone, indoline, isoindoline, chroman, tetralin and so forth. The aforementioned aromatic rings may have one to three substituents. When two or more substituents are present, they may be the same or different. Examples of the substituents include amino which may be substituted with lower alkyl or lower cycloalkyl; lower alkyl; lower alkoxy; hydroxyl; nitro; mercapto; cyano; lower alkylthio; halogen; a group represented by the formula —$a^a$—$b^a$ wherein $a^a$ represents a single bond, —$(CH_2)_k{}^a$—, —O—$(CH_2)_k{}^a$—, —S—$(CH_2)_k{}^a$— or —$N(R^{3a})$—$(CH_2)_k{}^a$— wherein $k^a$ is an integer of 1 to 5, and $R^{3a}$ represents a hydrogen atom or lower alkyl, and $b^a$ represents —$CH_2$—$d^a$ wherein $d^a$ represents amino which may be substituted with lower alkyl, a halogen atom, hydroxyl, lower alkylthio, cyano or lower alkoxy; a group represented by the formula —$a^a$—$e^a$—$f^a$ wherein $a^a$ has the same meaning as defined above, $e^a$ represents —S(O)— or —$S(O)_2$—, and $f^a$ represents amino which may be substituted with lower alkyl or lower alkoxy, lower alkyl, trifluoromethyl, —$(CH_2)_m{}^a$—$b^a$ or —$N(R^{4a})$—$(CH_2)_m{}^a$—$b^a$ wherein $b^a$ has the same meaning as defined above, $R^{4a}$ represents a hydrogen atom or lower alkyl, and $m^a$ is an integer of 1 to 5; a group represented by the formula —$a^a$—$g^a$—$h^a$ wherein $a^a$ has the same meaning as defined above, $g^a$ represents —C(O)— or —C(S)—, and $h^a$ represents amino which may be substituted with lower alkyl, hydroxyl, lower alkyl, lower alkoxy, —$(CH_2)_n{}^a$—$b^a$ or —$N(R^{5a})$—$(CH_2)_n{}^a$—$b^a$ wherein $b^a$ has the same meaning as defined above, $R^{5a}$ represents a hydrogen atom or lower alkyl, and $n^a$ is an integer of 1 to 5; a group represented by the formula —$a^a$—$N(R^{6a})$—$g^a$—$i^a$ wherein $a^a$ and $g^a$ have the same meanings as defined above, $R^{6a}$ represents a hydrogen atom or lower alkyl, and $i^a$ represents a hydrogen atom, a lower alkoxy group or $f^a$ ($f^a$ has the same meaning as defined above); a group represented by the formula —$a^a$—$N(R^{7a})$—$e^a$—$f^a$ wherein $a^a$, $e^a$ and $f^a$ have the same meanings as defined above, and $R^{7a}$ represents a hydrogen atom or lower alkyl; a group represented by the formula —$(CH_2)_p{}^a$—$j^a$—$(CH_2)_q{}^a$—$b^a$ wherein $j^a$ represents an oxygen atom or a sulfur atom, $b^a$ has the same meaning as defined above, and $p^a$ and $q^a$ may be the same or different and each represent an integer of 1 to 5; a group represented by the formula —$(CH_2)_u{}^a$—$Ar^a$ wherein $Ar^a$ represents phenyl or heteroaryl which may be substituted with lower alkyl, lower alkoxy or a halogen atom, and $u^a$ is an integer of 0 or 1 to 5; a group represented by the formula —CONH—$(CH_2)_u{}^a$—$Ar^a$ wherein $Ar^a$ and $u^a$ have the same meanings as defined above; a group represented by the formula —$SO_2$—$(CH_2)_u{}^a$—$Ar^a$ wherein $Ar^a$ and $u^a$ have the same meanings as defined above; and so forth.

In the compounds represented by the general formula (I), R preferably represents indole, quinoline or isoquinoline.

In the above general formula (I$^a$), the "monocyclic or bicyclic aromatic ring which may be substituted" represented by $A^a$ is an aromatic hydrocarbon ring or an aromatic heterocycle containing at least one of a nitrogen atom, an oxygen atom and a sulfur atom, each of which may have one to three substituents on the ring. Typical examples of the aromatic ring contained in $A^a$ include pyrrole, pyrazole, imidazole, thiophene, furan, thiazole, oxazole, benzene, pyridine, pyrimidine, pyrazine, pyridazine, naphthalene, quinoline, isoquinoline, phthalazine, naphthyridine, quinoxaline, quinazoline, cinnoline, indole, isoindole, indolizine, indazole, benzofuran, benzothiophene, benzoxazole, benzimidazole, benzopyrazole, benzothiazole and so forth. The aforementioned aromatic rings may have one to three substituents. When two or more substituents are present, they may be the same or different. Examples of the substituents include amino which may be substituted with lower alkyl or lower cycloalkyl; lower alkyl; lower alkoxy; hydroxyl; nitro; mercapto; cyano; lower alkylthio; halogen; a group represented by the formula —$a^a$—$b^a$ wherein $a^a$ represents a single bond, —$(CH_2)_k{}^a$—, —O—$(CH_2)_k{}^a$—, —S—$(CH_2)_k{}^a$— or —$N(R^{3a})$—$(CH_2)_k{}^a$— wherein $k^a$ is an integer of 1 to 5, and $R^{3a}$ represents a hydrogen atom or lower alkyl, and $b^a$ represents —$CH_2$—$d^a$ wherein $d^a$ represents amino which may be substituted with lower alkyl, halogen, hydroxyl, lower alkylthio, cyano or lower alkoxy; a group represented by the formula —$a^a$—$e^a$—$f^a$ wherein $a^a$ has the same meaning as defined above, $e^a$ represents —S(O)— or —$S(O)_2$—, and $f^a$ represents amino which may be substituted with lower alkyl or lower alkoxy, lower alkyl, trifluoromethyl, —$(CH_2)_m{}^a$—$b^a$ or —$N(R^{4a})$—$(CH_2)_m{}^a$—$b^a$ wherein $b^a$ has the same meaning as defined above, $R^{4a}$ represents a hydrogen atom or lower alkyl, and $m^a$ is an integer of 1 to 5; a group represented by the formula —$a^a$—$g^a$—$h^a$ wherein $a^a$ has the same meaning as defined above, $g^a$ represents —C(O)— or —C(S)—, and $h^a$ represents amino which may be substituted with lower alkyl, hydroxyl, lower alkyl, lower alkoxy, —$(CH_2)_n{}^a$—$b^a$ or —$N(R^{5a})$—$(CH_2)_n{}^a$—$b^a$ wherein $b^a$ has the same meaning as defined above, $R^{5a}$ represents a hydrogen atom or lower alkyl, and $n^a$ is an integer of 1 to 5; a group represented by the formula —$a^a$—$N(R^{6a})$—$g^a$—$i^a$ wherein $a^a$ and $g^a$ have the same meanings as defined above, $R^{6a}$ represents a hydrogen atom or lower alkyl, and $i^a$ represents a hydrogen atom, lower alkoxy or $f^a$ ($f^a$ has the same meaning as defined above); a group represented by the formula —$a^a$—$N(R^{7a})$—$e^a$—$f^a$ wherein $a^a$, $e^a$ and $f^a$ have the same meanings as defined above, and $R^{7a}$ represents a hydrogen atom or lower alkyl; a group represented by the formula —$(CH^2)_p{}^a$—$j^a$—$(CH_2)_q{}^a$—$b^a$ wherein $j^a$ represents an oxygen atom or a sulfur atom, $b^a$ has the same meaning as defined above, and $p^a$ and $q^a$ may be the same or different and each represent an integer of 1 to 5; a group represented by the formula —$(CH^2)_u{}^a$—$Ar^a$ wherein $Ar^a$ represents phenyl or heteroaryl which may be substituted with lower alkyl, lower alkoxy or halogen, and $u^a$ is 0 or an integer of 1 to 5; a group represented by the formula —CONH—$(CH_2)_u{}^a$—$Ar^a$ wherein $Ar^a$ and $u^a$ have the same meanings as defined above; a group represented by the formula —$SO^2$—$(CH_2)_u{}^a$—$Ar^a$ wherein $Ar^a$ and $u^a$ have the same meanings as defined above; and so forth.

In the aforementioned examples of the substituents, when the substituent is amino substituted with two alkyl groups, these alkyl groups may bond to form a 5- or 6-membered ring. Further, when $A^a$ is a nitrogen-containing heterocycle having hydroxyl or mercapto, these groups may present in the form of an oxo or thioxo group by resonance.

The "6-membered unsaturated hydrocarbon ring or unsaturated 6-membered heterocycle containing one nitrogen atom as a heteroatom, which may be substituted" represented by $B^a$ is benzene or pyridine which may be partially hydrogenated and may have one or two substituents on the ring. When two substituents are present, they may be the same or different.

The "5-membered heterocycle containing one or two nitrogen atoms which may be substituted" represented by $C^a$ is pyrrole, pyrazole or imidazole which may be partially hydrogenated and may have one or two substituents on the ring. When two substituents are present, they may be the same or different.

Examples of the substituents that $B^a$ and $C^a$ may have include, for example, halogen; cyano; lower alkyl; lower alkoxy; hydroxyl; oxo; a group represented by the formula —C(O)—$r^a$ wherein $r^a$ represents a hydrogen atom, amino which may be substituted with lower alkyl, lower alkyl, lower alkoxy or hydroxyl; amino which may be substituted with lower alkyl; trifluoromethyl; and so forth.

In the above general formula ($I^a$), the lower alkyl group in the definitions of $R^{1a}$ and $R^{2a}$ as well as the substituents that $A^a$, $B^a$ and $C^a$ may have means a linear or branched alkyl group having 1 to 6 carbon atoms. Examples thereof include methyl, ethyl, n-propyl, isopropyl, n-butyl, isobutyl, sec-butyl, tert-butyl, n-pentyl (amyl), isopentyl, neopentyl, tert-pentyl, 1-methylbutyl, 2-methylbutyl, 1,2-dimethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl and so forth. Among these, methyl, ethyl, n-propyl, isopropyl, n-butyl and isobutyl are preferred, and methyl, ethyl, n-propyl and isopropyl are most preferred among these.

The lower cycloalkyl group in the definitions of the substituents that $A^a$ may have is a cycloalkyl group having 3 to 8 carbon atoms, and examples thereof include cyclopropyl, cyclopentyl, cyclohexyl and so forth.

The lower alkoxy group in the definitions of the substituents that $A^a$, $B^a$ and $C^a$ may have means lower alkoxy derived from the aforementioned lower alkyl such as methoxy, ethoxy, n-propoxy, isopropoxy, n-butoxy, isobutoxy and tert-butoxy. Among these, methoxy and ethoxy are most preferred. The lower alkylthio means lower alkylthio derived from the aforementioned lower alkyl. Examples of the halogen atom include a fluorine atom, a chlorine atom, a bromine atom and so forth.

Among these, particularly preferred compounds include:
1) N-(3-cyano-4-methyl-1H-indol-7-yl)-3-cyanobenzenesulfonamide
2) N-(3-cyano-4-methyl-1H-indol-7-yl)-6-chloro-3-pyridinesulfonamide
3) N-(3-bromo-5-methyl-1H-indol-7-yl)-4-sulfamoylbenzenesulfonamide
4) N-(5-bromo-3-chloro-1H-indol-7-yl)-6-amino-3-pyridinesulfonamide
5) N-(3-bromo-5-methyl-1H-indol-7-yl)-3-cyanobenzenesulfonamide
6) N-(4-bromo-1H-indol-7-yl)-4-cyanobenzenesulfonamide
7) N-(4-chloro-1H-indol-7-yl)-6-amino-3-pyridinesulfonamide
8) N-(3-bromo-4-chloro-1H-indol-7-yl)-6-amino-3-pyridinesulfonamide
9) N-(3-bromo-5-methyl-1H-indol-7-yl)-5-cyano-2-thiophenesulfonamide
10) N-(4-bromo-3-chloro-1H-indol-7-yl)-2-amino-5-pyrimidinsulfonamide
11) N-(3-chloro-1H-indol-7-yl)-4-sulfamoylbenzenesulfonamide and so forth.

The sulfonamide derivative represented by the general formula (I$^a$) may form a salt with an acid or a base. The present invention also includes salts of the compounds represented by the general formula (I$^a$). Examples of the salt with an acid include salts with inorganic acids such as hydrochlorides, hydrobromides and sulfates and salts with organic acids such as acetic acid, lactic acid, succinic acid, fumaric acid, maleic acid, citric acid, benzoic acid, methanesulfonic acid and p-toluenesulfonic acid, and examples of the salt with a base include inorganic salts such as sodium salts, potassium salts and calcium salts and salts with organic bases such as triethylamine, arginine and lysine.

In the present invention, the "aromatic ring which may have one or two nitrogen atoms" represented by $Q^b$ means an aromatic hydrocarbon or a 6-membered aromatic heterocycle which contains one or two nitrogen atoms. Examples of the aromatic ring contained in $Q^b$ include benzene, pyridine, pyrimidine, pyrazine, pyridazine and so forth. Further, the "C5–C12 unsaturated monocyclic or polycyclic ring which may have 1 to 4 heteroatoms selected from a nitrogen atom, an oxygen atom and a sulfur atom" represented by M is an unsaturated monocyclic or polycyclic ring, which shares a double bond with $Q^b$. Examples thereof include aromatic hydrocarbons such as benzene and naphthalene, unsaturated hydrocarbons such as cyclopentene, cyclohexene, cycloheptene, cyclooctene, cyclopentadiene, cycloheptadiene and cyclooctadiene, and unsaturated heterocycles such as tetrahydropyridine, pyrrole, furan, thiophene, oxazole, isoxazole, thiazole, isothiazole, pyrazole, imidazole, triazole, pyridine, pyrimidine, pyrazine, pyridazine, triazine, indole, isoindole, quinoline, isoquinoline, indazolidine, naphthyridine, benzofuran, benzopyran, benzothiophene, benzimidazole, benzoxazole, benzothiazole, pyrrolopyridine, pyridopyrimidine and imidazopyridine. Further, the expression "$Q^b$ and $M^b$ may share one nitrogen atom" means the case where one nitrogen atom is contained at the condensation sites of the both rings. Examples of the ring formed in this manner include indazolidine, imidazo[1,2-a]pyridine, imidazo[1,5-a]pyridine, pyrazolo[1,5-a]pyrimidine and so forth.

In the present invention, the C1–C4 alkyl in $R^{1b}$, $R^{4b}$ and $R^{5b}$ or the C1–C4 alkyl in the C1–C4 alkyl which may be substituted with a halogen atom in $A^b$, $D^b$, $R^{1b}$, $R^{2b}$, $R^{3b}$, $R^{6b}$, $R^{7b}$, $R^{8b}$, $R^{9b}$, $R^{10b}$, $R^{11b}$, $R^{12b}$, $R^{13b}$, $R^{14b}$, $R^{15b}$, $G^{1b}$, $G^{2b}$ and Group A means a linear or branched alkyl group having 1 to 4 carbon atoms, and examples thereof include methyl, ethyl, n-propyl, isopropyl, n-butyl, isobutyl, sec-butyl and tert-butyl. The expression "may be substituted with a halogen atom" means that these alkyl groups may be substituted with a halogen atom selected from a fluorine atom, a chlorine atom, a bromine atom and an iodine atom. Examples include monofluoromethyl, monochloromethyl, difluoromethyl, trifluoromethyl, 1- or 2-monofluoroethyl, 1- or 2-monochloroethyl, 1- or 2-monobromoethyl, 1,2-difluoroethyl, 1,2-dichloroethyl, 1,1,2,2,2-pendafluoroethyl, 3,3,3-trifluoropropyl and so forth. Among these, monofluoromethyl, difluoromethyl, trifluoromethyl, 1- or 2-monofluoroethyl, 1,2-difluoroethyl, 1,1,2,2,2-pentafluoroethyl and so forth are preferred.

In the present invention, the C1–C4 alkoxy in the C1–C4 alkoxy which may be substituted with a halogen atom in $A^b$, $D^b$ and Group A means a linear or branched alkoxy having 1 to 4 carbon atoms. Examples thereof include methoxy, ethoxy, n-propyloxy, isopropyloxy, n-butyloxy, isobutyloxy, sec-butyloxy and tert-butyloxy. The expression "may be substituted with a halogen atom" means that the alkoxy may be substituted with a halogen atom selected from a fluorine atom, a chlorine atom, a bromine atom and an iodine atom. Examples include monofluoromethoxy, difluoromethoxy, trifluoromethoxy, 1- or 2-monofluoroethoxy, 1- or 2-monochloroethoxy, 1- or 2-monobromoethoxy, 1,2-difluoroethoxy, 1,1,2,2,2-pentafluoroethoxy, 3,3,3-trifluoropropyloxy and so forth. Among these, monofluoromethoxy, difluoromethoxy, trifluoromethoxy, 1- or 2-monofluoroethoxy, 1,2-difluoroethoxy, 1,1,2,2,2-pentafluoroethoxy and so forth are preferred.

In the present invention, the C2–C4 alkenyl or alkynyl which is present in $A^b$ and $D^b$ means alkenyl or alkynyl having 2 to 4 carbon atoms. Examples thereof include vinyl, allyl, 2- or 3-butenyl, 1,3-butadienyl, ethynyl, 2-propynyl, 2-methylethynyl, 2- or 3-butynyl and so forth.

In the present invention, the aryl which is present in $B^b$ and Group A means an aromatic hydrocarbon. Examples thereof include phenyl, naphthyl and so forth. Further, the heteroaryl is a monocyclic or polycyclic ring containing one or more atoms of nitrogen, oxygen and sulfur. Examples thereof include pyrrolyl, imidazolyl, pyrazolyl, triazolyl, furyl, thienyl, oxazolyl, isoxazolyl, thiazolyl, isothiazolyl, thiadiazolyl, pyridyl, pyrimidyl, pyrazyl, indolyl, indolizinyl, benzoimidazolyl, benzothiazolyl, benzoxazolyl, quinolinyl, isoquinolinyl, quinazolinyl, phthalazinyl and so forth.

In the present invention, the expression "$R^{8b}$ and $R^{9b}$ may form a 5- or 6-membered ring together with a nitrogen atom to which they bond, and the ring may further contain a nitrogen atom, an oxygen atom or a sulfur atom" in the definitions of $R^{8b}$ and $R^{9b}$ means that $R^{8b}$ and $R^{9b}$ may form pyrrolidinyl, piperidinyl, morpholino, thiomorpholino, piperazinyl or the like together with the nitrogen atom to which they bond.

In the present invention, the alkyl in the aminosulfonyl which may be substituted with mono- or di(C1–C4 alkyl), (C1–C4 alkyl)-S(O)$_s{}^b$—(C1–C4 alkylene), C1–C4 alkyl or phenylsulfonylamino which may be substituted and the C1–C4 alkyl which may be substituted with C1–C4 alkyl in Group A mean the same alkyl groups defined as above. Examples of the alkylene include methylene, ethylene, propylene, butylene, methylmethylene, 1- or 2-methylethylene, 1-, 2- or 3-methylpropylene, dimethylmethylene and so forth.

Further, the C1–C8 alkanoyl means formyl, acetyl, propionyl, butyryl, isobutyryl, valeryl, benzoyl or the like.

In the present invention, the protective group in the "amino group which may have a protective group" present in $J^b$ is not particularly limited so long as the group is known as a protective group of amino for usual organic synthesis. Examples thereof include benzyloxycarbonyl, t-butoxycarbonyl, formyl, acetyl, chloroacetyl, 2,2,2-trichloroethyl, benzylidene, benzhydryl, trityl and so forth. Further, the protective group in the carboxy which may have a protective group and the protective group of the carboxy in $R^{16b}$ are not particularly limited so long as the groups are known as a protective group of carboxy in usual organic synthesis. Examples thereof include methyl, ethyl, propyl, isopropyl, t-butyl, methoxymethyl, 2,2,2-trichloroethyl, pivaloyloxymethyl, benzyl and so forth.

In the present invention, examples of the substituent for the expression "which may be substituted" or "which may have a substituent" include a halogen atom; C1–C4 alkyl or alkoxy which may be substituted with a halogen atom; hydroxyl; hydroxy(C1–C4 alkyl); amino which may be substituted with mono- or di-(C1–C4 alkyl); C2–C4 alkenyl or alkynyl; cyano; C1–C8 acyl; aminosulfonyl which may be substituted with mono- or di-(C1–C4 alkyl); carboxy;

(C1–C4 alkoxy)carbonyl; carbamoyl which may be substituted with mono- or di-(C1–C4 alkyl); and so forth.

The heterocyclic compounds containing sulfonamide represented by the general formula ($I^b$) may form a salt with an acid or a base. The present invention also includes salts of the compounds represented by the general formula ($I^b$). Examples of the salt with an acid include salts with inorganic acids such as hydrochlorides, hydrobromides and sulfates and salts with organic acids such as acetic acid, lactic acid, succinic acid, fumaric acid, maleic acid, citric acid, benzoic acid, methanesulfonic acid and p-toluenesulfonic acid. Further, examples of the salt with a base include inorganic salts such as sodium salts, potassium salts and calcium salts and salts with organic bases such as triethylamine, arginine and lysine.

Hydrates as well as optical isomers of these compounds, if present, are of course all included in the scope of the compounds. Further, compounds which are formed in vivo from these compounds by metabolism such as oxidation, reduction, hydrolysis and conjugation and exhibit angiogenesis inhibitory action are also included. Further, the present invention also includes compounds which undergo metabolism such as oxidation, reduction and hydrolysis in vivo to produce the compounds of the present invention.

The compounds for use in the present invention can be produced by various methods. For example, some of the methods are specifically disclosed in Japanese Patent Laid-open Publication (Kokai) Nos. 7-165708 and 8-231505.

Exemplification

The present invention will be explained more specifically with reference to the following Examples. However, the scope of the present invention is not limited to them.

REFERENCE EXAMPLE 1

Effect of Compound A on Integrin α2 Expression

Human umbilical vein endothelial cells (HUVEC) were isolated from human umbilical cord and cultured in EGM medium (2% FCS, hydrocortisone free, Clonetics). The cells were subcultured in a type-I collagen-coated flask (Sumilon), and the fourth to sixth subcultures were used. The anti-human integrin α2 antibody (A2-IIE10) was purchased from Upstate Biotechnology Inc. The anti-human CD31 antibody (JC/70A) and an FITC-labeled F(ab')$_2$ fragment of rabbit anti-mouse immunoglobulin were purchased from Dako.

Figure 1:
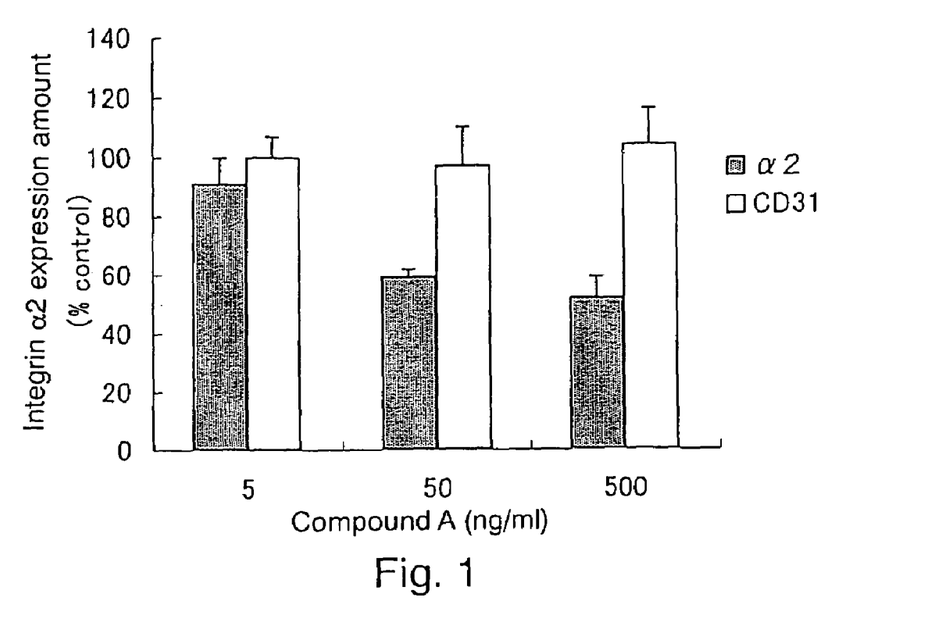
FIG. 1 shows the effect of Compound A on integrin α2 expression.

The cells were inoculated in a 25-cm$^2$ flask for cell culture and cultured at 37° C. in a CO$_2$ incubator. After 3 hours, the medium was replaced with the same medium containing Compound A (5, 50, 500 ng/ml) and further cultured for 48 hours. The cells were collected, and 2×10$^5$ cells were floated in 100 μl of PBS (0.1% BSA, 0.05% NaN$_3$). 1 μg of the primary antibody was added, and the cells were incubated at 4° C. for 30 minutes, washed with PBS and then incubated with the FITC-labeled secondary antibody for 30 minutes. The cells were washed with PBS and then immobilized with CellFix (Becton Dickinson). The fluorescence value of 2×10$^4$ cells of each sample was measured by using FACS Calibur (Becton Dickinson). The expression amount of the cell surface molecule was obtained by correcting the fluorescence value of each sample using the fluorescence value of the control sample, which did not contain the primary antibody (following equation):

RMFI (relative mean fluorescence intensity)=Sample MFI (mean fluorescence intensity)/Background MFI As shown in FIG. 1, Compound A (50, 500 ng/ml) decreased the integrin α2 expression amount on HUVEC.

REFERENCE EXAMPLE 2

Influence of Anti-Integrin α2 Antibody and Compound A on Tube Formation

Type-I collagen gel was placed in each well of a 24-well plate and gelled, and HUVEC suspended in a serum-free medium (Human Endothelial-SFM Basal Growth Medium, GIBCO BRL) containing 10 ng/ml of EGF (GIBCO BRL) and 20 ng/ml of bFGF (GIBCO BRL) or 20 ng/ml of VEGF (Wako Pure Chemical Industries) were inoculated at a density of 1 to 1.2×10$^5$ cells/well. The cells were cultured overnight at 37° C., and overlaid with type-I collagen gel for gelation. Then, the aforementioned serum-free medium (containing EGF and bFGF or VEGF) containing a drug (anti-integrin α2 antibody or Compound A) was added and the cells were further cultured at 37° C. for 4 days. For the action of the anti-integrin α2 antibody, the experiment was conducted by using a 96-well plate.

After the culture, the cells were colored with MTT, and the tubes formed by HUVEC were photographed under a microscope. The photograph was electronized by a scanner, and the tube formation by HUVEC was quantified by measuring the lengths of the tubes by using image analysis software, Mac SCOPE 2.56 (MITANI).

Figure 2:
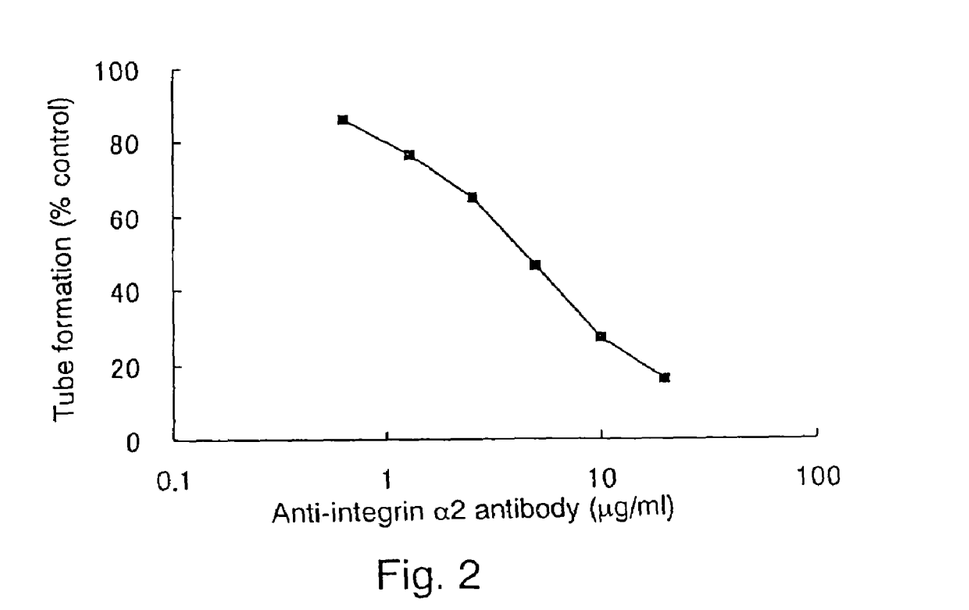
FIG. 2 shows the influence of an anti-integrin α2 antibody on tube formation.
Figure 3:
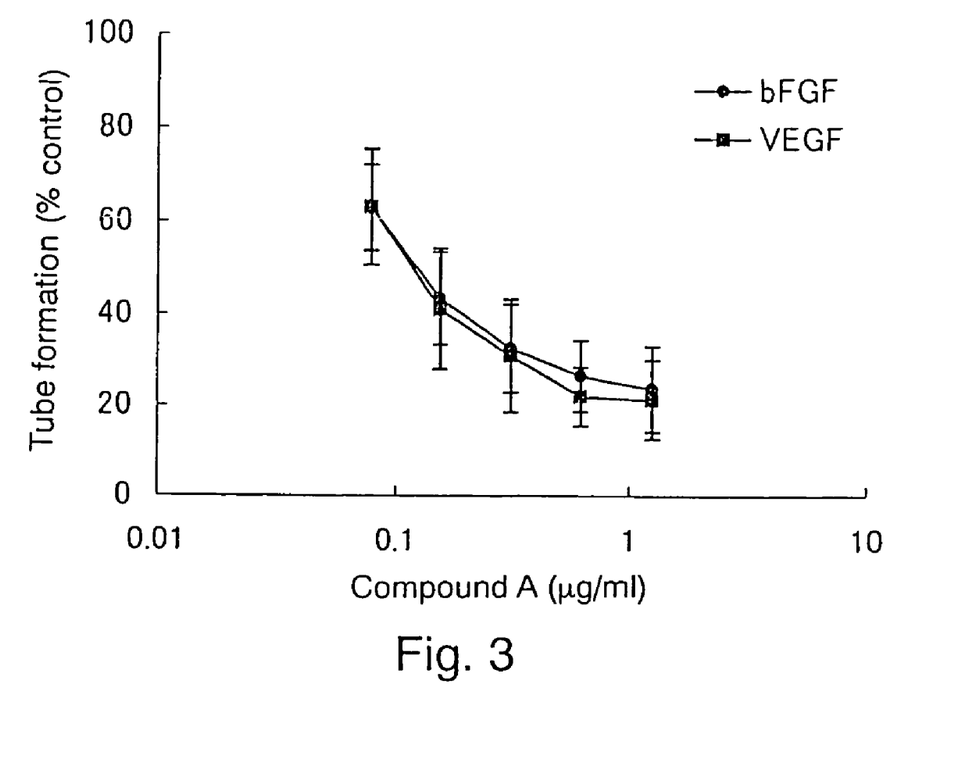
FIG. 3 shows the influence of Compound A on tube formation.

As shown in FIG. 2, it was revealed that the anti-integrin α2 antibody inhibited the tube formation of HUVEC induced by bFGF, indicating that integrin α2 was involved in the tube formation induced by bFGF. Further, as shown in FIG. 3, Compound A inhibited the tube formation of HUVEC induced by bFGF or VEGF. Along with the results of Reference Example 2, it was considered that Compound A inhibited the tube formation by inhibiting the integrin α2 expression.

EXAMPLE 1

Correlation of Tumor Volume Increase Inhibitory Action and Platelet Integrin α2 Expression Inhibitory Action of Compound A 100 μl of suspension of KP-1 (human pancreatic cancer cell strain) in PBS (5×10$^7$ cells/ml) was transplanted into the subcutis of a mouse (SLC KSN, female, Lot. No. 085605376). From one week after the transplantation, 0.5% methylcellulose aqueous solution (vehicle) or 100 or 200 mg/kg of Compound A (suspension in 0.5% methylcellulose) was orally administered twice a day. The body weight and the tumor volume were measured in a daily time course. The mouse was anesthetized with diethyl ether, and blood was collected from ocular fundus by using a capillary tube in a daily time course. 4 μl of blood was diluted with 396 μl of PBS containing 0.0038% sodium citrate aqueous solution. FITC-labeled anti-mouse CD49b antibody (Pharmingen, Cat. No. 09794D, Lot. No. M006073) was diluted 30 times with PBS containing 0.1% BSA. 10 μl of the antibody was added to 90 μl of the diluted blood. The mixture was allowed to react at room temperature for 60 minutes and passed through a filter (FALCON, Cat. No.2235). The residue was added with 900 μl of PBS, and a platelet fraction was separated based on forward scattering light and side scattering light by using a flow cytometer (Becton Dickinson, FACS Calibur), and the fluorescence intensity on the platelets was measured.

Figure 4:
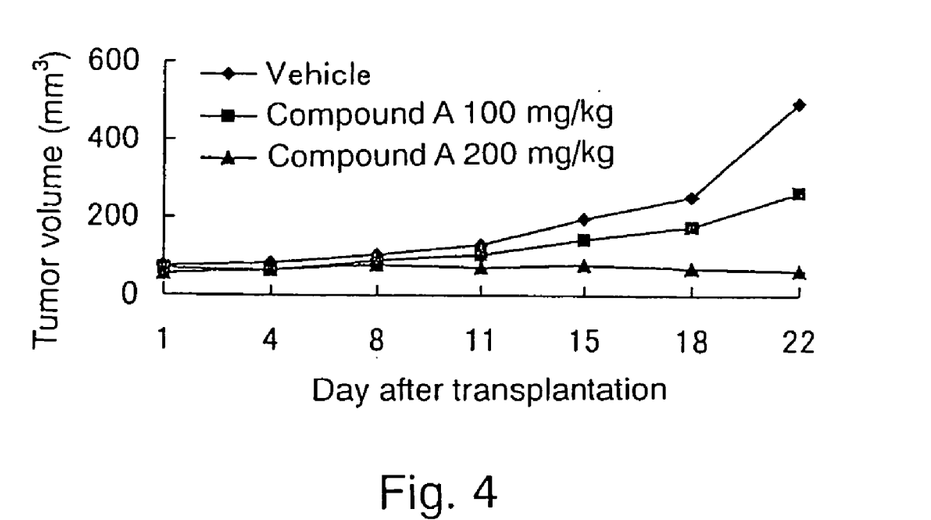
FIG. 4 shows an inhibitory action of Compound A on tumor volume increase.

As shown in FIG. 4, Compound A inhibited the KP-1 tumor volume increase at doses of 100 mg/kg and 200 mg/kg. Along with the results of Reference Examples 1 and 2, it was concluded that Compound A inhibited tube formation by inhibiting integrin α2 expression, and also inhibited the angiogenesis induced by tumor, resulting in inhibition of the tumor volume increase.

Figure 5:
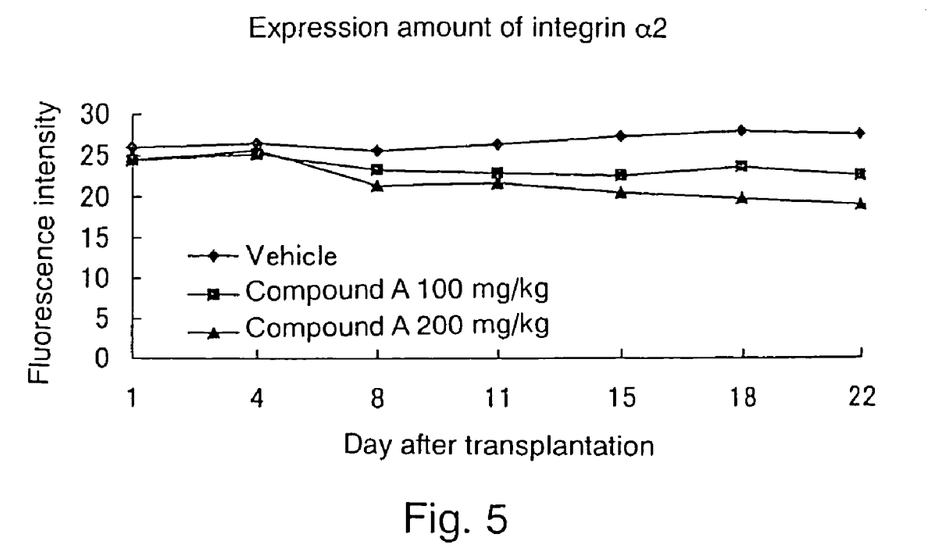
FIG. 5 shows the influence of Compound A on integrin α2 expression in platelets.

As shown in FIG. 5, Compound A decreased the amount of integrin α2 in platelets measured at the same time. The decrease of the integrin α2 expression in platelets was observed at doses of 100 mg/kg and 200 mg/kg, at which point inhibition of the tumor volume increase was observed. Thus, it was demonstrated that the integrin α2 expression amount in platelets could be used as a surrogate marker of the tumor volume increase inhibitory action of Compound A.

Applications

According to the present invention, it becomes possible to monitor efficacy of a drug, for example, an angiogenesis inhibitor, which exhibits its drug efficacy by inhibiting integrin expression, by using integrin expression amount in platelets as a surrogate marker. Since platelets can be easily collected as a sample, efficient monitoring becomes possible.

What is claimed is:

1. A method comprising steps of:
measuring an integrin expression amount in platelets of an individual who has received a drug; and
based on the measured integrin expression amount, determining what effect the drug has on integrin expression in cells other than platelets.

2. The method according to claim 1, wherein the integrin is integrin α2.

3. The method according to claim 1, wherein the integrin expression amount is measured by an immunochemical method.

4. The method according to claim 3, wherein the immunochemical method is flow cytometry.

5. The method according to claim 1, wherein the integrin expression amount is measured by measuring an amount of mRNA coding for the integrin.

6. The method according to claim 5, wherein the amount of mRNA is measured by quantitative PCR.

7. The method according to claim 2, wherein the drug is a sulfonamide compound represented by the general formula (I):

wherein
B represents a C6–C10 aryl ring or a 6- to 10-membered heteroaryl ring, each of which may be substituted and partially saturated;
K represents a single bond, —CH═CH— or —(CR$^{4b}$R$^{5b}$)$_m{}^b$— wherein R$^{4b}$ and R$^{5b}$ may be the same or different and each represent a hydrogen atom or C1–C4 alkyl, and m$^b$ is an integer of 1 or 2;
R$^1$ represents a hydrogen atom or C1–C6 alkyl;
Z represents a single bond or —CO—NH—; and
R represents a C6–C10 aryl ring or a 6- to 10-membered heteroaryl ring, each of which may be substituted and partially saturated; or
a pharmacologically acceptable salt thereof, or a hydrate thereof.

8. The method according to claim 7, wherein R represents indole, quinoline or isoquinoline.

9. The method according to claim 2, wherein the drug is a sulfonamide compound represented by the general formula (I$^a$):

wherein
A$^a$ represents a monocyclic or bicyclic aromatic ring which may be substituted;
B$^a$ represents a 6-membered unsaturated hydrocarbon ring or an unsaturated 6-membered heterocycle containing one nitrogen atom as a heteroatom, each of which may be substituted;
C$^a$ represents a 5-membered heterocycle containing one or two nitrogen atoms which may be substituted;
R$^{1a}$ represents a hydrogen atom or C1–C6 alkyl;
W$^a$ represents a single bond or —CH═CH—;
Y$^a$ represents a carbon or nitrogen atom;
Z$^a$ represents —N(R$^{2a}$)— wherein R$^{2a}$ represents a hydrogen atom or lower alkyl, or a nitrogen atom; or
a pharmacologically acceptable salt thereof, or a hydrate thereof.

10. The method according to claim 9, wherein W$^a$ represents a single bond.

11. The method according to claim 9, wherein W$^a$ represents a single bond, Z$^a$ represents —NH—, and Y$^a$ represents a carbon atom.

12. The method according to claim 9, wherein B$^a$ represents benzene or pyridine which may be substituted.

13. The method according to claim 9, wherein C$^a$ represents pyrrole which may be substituted.

14. The method according to claim 9, wherein A$^a$ represents benzene or pyridine which may be substituted, B$^a$ represents benzene which may be substituted, C$^a$ represents pyrrole which may be substituted, W$^a$ represents a single bond, and Z$^a$ represents —NH—.

15. The method according to claim 2, wherein the drug is a heterocyclic compound containing sulfonamide represented by the general formula (I$^b$):

wherein
  $A^b$ represents a hydrogen atom; a halogen atom; hydroxyl; C1–C4 alkyl or alkoxy which may be substituted with a halogen atom; cyano; —(CO)$_k{}^b$NR$^{2b}$R$^{3b}$ wherein R$^{2b}$ and R$^{3b}$ may be the same or different and each represent a hydrogen atom or C1–C4 alkyl which may be substituted with a halogen atom, and k$^b$ is 0 or 1; C2–C4 alkenyl or alkynyl which may be substituted; or phenyl or phenoxy which may have a substituent selected from Group A mentioned below;
  $B^b$ represents aryl or monocyclic heteroaryl which may have a substituent selected from Group A mentioned below, or wherein $Q^b$ represents an aromatic ring which may have one or two nitrogen atoms, $M^b$ represents a C5–C12 unsaturated monocyclic or polycyclic ring sharing a double bond with $Q^b$, which may have one to four heteroatoms selected from a nitrogen atom, an oxygen atom and a sulfur atom, $Q^b$ and $M^b$ may share a nitrogen atom, and $Q^b$ and $M^b$ may have a substituent selected from Group A mentioned below;
  $K^b$ represents a single bond or —(CR$^{4b}$R$^{5b}$)m$^b$— wherein R$^{4b}$ and R$^{5b}$ may be the same or different and each represent a hydrogen atom or C1–C4 alkyl, and m$^b$ is an integer of 1 or 2;
  $T^b$, $W^b$, $X^b$ and $Y^b$ may be the same or different and each represent =C(D$^b$)— wherein D$^b$ represents a hydrogen atom, a halogen atom, hydroxyl, C1–C4 alkyl or alkoxy which may be substituted with a halogen atom, cyano, —(CO)$_n{}^b$NR$^{6b}$R$^{7b}$ wherein R$^{6b}$ and R$^{7b}$ may be the same or different and each represent a hydrogen atom or C1–C4 alkyl which may be substituted with a halogen atom, and n$^b$ is 0 or 1, or C2–C4 alkenyl or alkynyl which may be substituted; or a nitrogen atom;
  $U^b$ and $V^b$ may be the same or different and each represent =C(D$^b$)— wherein D$^b$ has the same meaning as defined above, a nitrogen atom, —CH$_2$—, an oxygen atom or —CO—;
  $Z^b$ represents a single bond or —CO—NH—;
  $R^{1b}$ represents a hydrogen atom or C1–C4 alkyl;
  — represents a single bond or a double bond:
  Group A: a halogen atom; hydroxyl; C1–C4 alkyl or alkoxy which may be substituted with a halogen atom; cyano; —R$^{8b}$R$^{9b}$N(NH)$_p{}^b$— wherein R$^{8b}$ and R$^{9b}$ may be the same or different and each represent a hydrogen atom or C1–C4 alkyl which may be substituted with a halogen atom, and p$^b$ is 0 or 1, R$^{8b}$ and R$^{9b}$ may form a 5- or 6-membered ring together with a nitrogen atom to which they bond, and this ring may further contain a nitrogen atom, an oxygen atom or a sulfur atom and may be substituted; aminosulfonyl which may be substituted with mono- or di-(C1–C4 alkyl); C1–C8 acyl which may be substituted; (C1–C4 alkyl)-S(O)$_s{}^b$—(C1–C4 alkylene) wherein s$^b$ is an integer of 0, 1 or 2; C1–C4 alkyl or phenylsulfonylamino which may be substituted; —(CO)$_q{}^b$NR$^{10b}$R$^{11b}$ wherein R$^{10b}$ and R$^{11b}$ may be the same or different and each represent a hydrogen atom or C1–C4 alkyl which may be substituted with a halogen atom or amino which may be substituted with C1–C4 alkyl, and q$^b$ is 0 or 1; or aryl or heteroaryl which may be substituted; or
  a pharmacologically acceptable salt thereof, or a hydrate thereof.

16. The method according to claim 15, wherein $U^b$ and $V^b$ each represent =C(D$^b$)— wherein D$^b$ has the same meaning as defined above, or a nitrogen atom.

17. The method according to claim 15, wherein $Z^b$ represents a single bond.

18. The method according to claim 15, wherein at least one of $T^b$, $U^b$, $V^b$, $W^b$, $X^b$ and $Y^b$ represents a nitrogen atom.

19. The method according to claim 15, wherein $A^b$ represents a halogen atom; C1–C4 alkyl or alkoxy which may be substituted with a halogen atom; cyano; —(CO)$_r{}^b$NR$^{12b}$R$^{13b}$ wherein R$^{12b}$ and R$^{13b}$ may be the same or different and each represent a hydrogen atom or C1–C4 alkyl which may be substituted with a halogen atom, and r$^b$ is 0 or 1; or C2–C4 alkenyl or alkynyl which may be substituted.

20. The method according to 15, wherein only one of $T^b$, $U^b$, $V^b$, $W^b$, $X^b$, and $Y^b$ represents a nitrogen atom.

21. The method according to claim 15, wherein only one of $T^b$, $W^b$ and $Y^b$ represents a nitrogen atom.

22. The method according to claim 1, wherein the cells other than platelets are cells of a tissue in which angiogenesis can occur, and the influence on integrin expression is determined as angiogenesis inhibitory action.

23. The method according to claim 1, wherein the cells other than platelets are tumor cells, and the influence on integrin expression is determined as tumor growth inhibitory action.

24. The method according to claim 1, wherein the drug is N-(3-cyano-4-methyl-1H-indol-7-yl)-3-cyanobenzenesulfonamide, or a pharmacologically acceptable salt thereof or a hydrate thereof.

* * * * *